(12) United States Patent
Okauchi et al.

(10) Patent No.: US 6,506,416 B1
(45) Date of Patent: Jan. 14, 2003

(54) VIRUCIDE COMPOSITION AND SPORICIDE COMPOSITION

(75) Inventors: Yuji Okauchi, Wakayama (JP); Tadashi Moriyama, Wakayama (JP); Hiroyoshi Hiramatsu, Wakayama (JP); Yuichi Hioki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/606,933

(22) Filed: Jun. 30, 2000

(30) Foreign Application Priority Data

Jun. 30, 1999 (JP) ............................. 11-185099
Jun. 30, 1999 (JP) ............................. 11-185100

(51) Int. Cl.⁷ ..................... A01N 59/00; A01N 37/20
(52) U.S. Cl. ..................... 424/615; 424/613; 424/614; 424/616; 514/714; 514/970; 514/973; 514/626; 422/28; 422/29
(58) Field of Search ................. 424/613–616; 514/714, 626, 970, 973; 422/28, 29

(56) References Cited

U.S. PATENT DOCUMENTS 4,938,889 A * 7/1990 Wilsberg et al. ............ 252/102

FOREIGN PATENT DOCUMENTS

| DE | A13615787 | 11/1987 |
| DE | A119651415 | 6/1998 |
| EP | A20096525 | 12/1983 |
| EP | A20268170 | 5/1988 |
| EP | 427314 | * 5/1991 |
| JP | A-6263504 | 3/1987 |
| WO | 9406294 | 3/1994 |
| WO | A19424869 | 11/1994 |
| WO | A19520876 | 8/1995 |
| WO | A19618297 | 6/1996 |
| WO | A19957980 | 11/1999 |

OTHER PUBLICATIONS

List of Culture, Microorganisms Tenth Edition pp. 131 (1996).
Chemical Abstracts 109:156315, 1988.*

* cited by examiner

*Primary Examiner*—John Pak
(74) *Attorney, Agent, or Firm*—Birch, Stewart, Kolasch & Birch, LLP

(57) ABSTRACT

The present invention provides a virucide composition and/or sporicide composition having a high virucidal effect and sporicidal effect and being excellent in safety and workability. That is, the present invention provides a virucide composition and/or sporicide composition comprising (a) an inorganic peroxide, (b) tetraacetylethylenediamine and (c) at least one selected from a salt of an alkaline metal salt with an inorganic acid and a salt of an alkaline earth metal with an inorganic acid in a specific ratio.

17 Claims, No Drawings

VIRUCIDE COMPOSITION AND SPORICIDE COMPOSITION

TECHNICAL FIELD

The present invention relates to a virucide composition and/or a sporicide composition.

PRIOR ART

Some species of bacillus produce tough spores (endospores) called bacterial spores. It has been known that a spore has a high resistance to a toxic action including a high temperature by heat, a drying, a drug and others and that even those which had been dormant for several years to several ten years has its regenerative ability. Therefore, in a field such as a medicine and a food industry, it becomes one of the standards for the sterilization that spores are completely killed.

In the case of a medical instrument and a furnishing used in a hospital, a protective institution and so on, it is necessary to fully carry out the germicidal deterging treatment from the viewpoint of prevention of infection and the like in the hospital and so on. There have been known various germicides, disinfectants, etc. to carry out the germicidal deterging treatment in a such way as above-mentioned one.

For example, in JP-A 62-63504, a germicide composition containing a cationic surfactant, an inorganic peroxide and an activator for the inorganic peroxide is disclosed. However, for the treatment of a spore having a strong resistance to drugs, common germicides are insufficient and, therefore, glutaraldehyde and peracetic acid having a broad antibacterial spectrum have been used.

In addition, for the treatment of a virus having a strong resistance to drugs, a germicide for common germ is insufficient and, therefore, glutaraldehyde and peracetic acid having a broad antibacterial spectrum have been used. Further, it is disclosed in JP-A 8-502047 that an aqueous solution containing an aliphatic peracid and the corresponding aliphatic acid in a specific molar ratio and containing hydrogen peroxide is used as a virucide.

Examples of the germicidal deterging treatment using glutaraldehyde and/or peracetic acid include that, in case of a germicidal deterging of an endoscope, a sterilizing treatment is carried out by means of glutaraldehyde and/or peracetic acid after a primary disinfection using a germicide of a quaternary ammonium salt type, an alcohol, a super-oxidized water, an amphoteric surfactant, etc. and/or a deterging step using an enzyme preparation, a neutral detergent, etc. and, if necessary, a disinfection in an autoclave and/or a dry sterilization by heat is carried out.

However, the above-mentioned treatment takes so long time, therefore there has been a demand for further reduction and simplification of the steps. At that time, it is necessary that a reliable virucidal effect and/or sporicidal effect is obtained. In addition, glutaraldehyde has a problem that it generates toxic gas of aldehyde to deteriorate the working environment and that it reacts with protein adhering to the medical instrument, etc. to generate a firmly adhesive matters making the deterging difficult. On the other hand, peracetic acid has a strong irritating smell and a strong oxidizing property, therefore it is feared that the peracetic acid erodes a container thereof, a treated matter thereby, etc. depending upon the material used therefor. An aqueous solution containing peracid and hydrogen peroxide as mentioned in JP-A 8-502047 has the same problem, too.

An object of the present invention is to obtain a reliable virucidal effect and/or sporicidal effect by a simple treatment and also to obtain a virucide and/or sporicide composition being excellent in safety and workability.

DISCLOSURE OF THE INVENTION

The present invention provides a virucide and/or sporicide composition comprising (a) an inorganic peroxide, (b) tetraacetylethylenediamine and (c) at least one selected from a salt of an alkaline metal with an inorganic acid and a salt of an alkaline earth metal with an inorganic acid at the ratio of (a)/(b) by weight being from 10/1 to 1/2.

The inorganic peroxide (a) is preferably sodium percarbonate. The composition may comprise (d) at least one surfactant selected from the group consisting of a nonionic surfactant, an anionic surfactant, an amphoteric surfactant and a cationic surfactant.

The present invention further provides a method of killing a virus, which comprises applying an aqueous solution containing the above-mentioned composition on a place where a virus should be killed. The present invention furthermore provides use of the above-mentioned composition as a virucide or for manufacturing a virucide. The present invention may also provide a virucidal method which comprise bringing an aqueous solution containing the above-mentioned composition and having pH 2 to 9 into contact with a virus. The present invention may also provide use of an aqueous solution, which contains the above-mentioned composition and which has pH 2 to 9, being brought into contact with a virus as a virucide.

Then, the present invention provides a method of killing a spore, which comprises applying an aqueous solution containing the above-mentioned composition on a place where a spore should be killed. The present invention furthermore provides use of the above-mentioned composition as a sporicide or for manufacturing a sporicide. The present invention may also provide a sporicidal method which comprise bringing an aqueous solution containing the above-mentioned composition and having pH 2 to 9 into contact with a spore. The present invention may also provide use of an aqueous solution, which contains the above-mentioned composition and which has pH 2 to 9, being brought into contact with a spore as a sporicide.

Incidentally, it is preferable that (a)/(c) is from 1/1 to 4/1.

It is further preferable that (a)/(b) is from 1/1 to 2/1, (a)/(c) is from 1/1 to 4/1 and (b)/(d) is from 20/1 to 2/1.

The present invention inhibits the generation of a toxic gas and an irritating smell, therefore it is excellent in safety and workability. And then, it is excellent in resistance to drugs as well.

MODES FOR CARRYING OUT THE INVENTION

With regard to the inorganic peroxide (a) used in the present invention, sodium percarbonate, sodium perborate, etc. may be exemplified and sodium percarbonate is preferable. Then, the ratio of the component (a) to tetraacetylethylenediamine (b), i.e. (a)/(b), by weight is from 10/1 to 1/2, preferably from 3/1 to 1/1 and particularly preferably from 2/1 to 1/1 from the viewpoint of the virucidal effect and/or the sporicidal effect.

Further, the salt of the alkali metal with the inorganic acid and/or of the alkali earth metal with the inorganic acid (c), which is used for the present invention, includes sodium sulfate, sodium nitrate, sodium chloride, sodium carbonate, sodium hydrogen carbonate, magnesium sulfate, magnesium nitrate, magnesium chloride and magnesium carbonate. Among them, sodium sulfate or magnesium sulfate is preferable. It is preferable that the component (c) is used in an amount as compared with the inorganic peroxide (a) in terms of the ratio by weight of (a)/(c) of from 1/1 to 4/1. Each of the salts of the alkali metal with the inorganic acid and of the alkali earth metal with the inorganic acid may be used solely. However, they are preferably combined and used from the viewpoint of drying the inorganic peroxide and improving the virucidal activity and the sporicidal activity.

It is preferable that the composition of the present invention comprises (d) at least one surfactant which is selected from the group consisting of a nonionic surfactant, an anionic surfactant, an amphoteric surfactant and a cationic surfactant.

The nonionic surfactant includes a polyoxyethylene alkyl ether, a polyoxyethylene alkylene ether, a polyoxyethylene sorbitan fatty acid ester, an alkyl polyglycoside, a sucrose fatty acid ester and an alkyl polyglycerol ether. Among them, a polyoxyethylene (the average number of added ethylene oxide being 2 to 300) alkyl (the number of carbon atoms being 12 to 18) ether is preferable.

The anionic surfactant includes a higher fatty acid salt, a higher alcohol sulfate salt, a higher alcohol sulfonate, a sulfated fatty acid salt, a sulfonated fatty acid salt, a phosphate salt, a sulfate salt of a fatty acid ester, a sulfonate salt of a fatty acid ester, a sulfate salt of a higher alcohol ether, a sulfonate salt of a higher alcohol ether, an acetate substituted with a higher alcohol ether, a condensation product of a fatty acid with an amino acid, an alkylolated sulfate salt of a fatty acid amide, an alkylated sulfonate salt of a fatty acid amide, a sulfosuccinate salt, an alkylbenzene sulfonate, an alkylphenol sulfonate, an alkylnaphthalene sulfonate, an alkylbenzimidazole sulfonate, an amidoether carboxylic acid or a salt thereof, an ether carboxylic acid or a salt thereof, N-acyl-N-methyltaurine or a salt thereof, an amidoether sulfuric acid or a salt thereof, an N-acylglutamic acid or a salt thereof, an N-amidoethyl-N-hydroxyethylacetic acid or a salt thereof, an acyloxyethanesulfonic acid or a salt thereof, an N-acyi-p-alanine or a salt thereof, an N-acyl-N-carboxyethyltaurine or a salt thereof, an N-acyl-N-carboxyethylglycine or a salt thereof and an alkyl or alkenyl-aminocarbonylmethylsulfuric acid or a salt thereof. Among them, a higher alcohol sulfate salt is preferable.

Then, the amphoteric surfactant includes an amine oxide such as an alkyldimethylamine oxide and a betaine such as an alkyldimethylaminofatty acid betaine and an alkylcarboxymethylhydroxyethylimidazolium betaine. A betaine is preferable.

The cationic surfactant includes an alkyl trimethyl ammonium salt such as lauryl trimethyl ammonium chloride, stearyl trimethyl ammonium chloride and cetyl trimethyl ammonium chloride; a dialkyl dimethyl ammonium salt such as distearyl dimethyl ammonium chloride and a dialkyl ($C_{12}$–$C_{18}$) dimethyl ammonium chloride; an alkyl dimethyl benzyl ammonium salt such as an alkyl ($C_{12}$–$C_{14}$) dimethyl benzyl ammonium chloride; a substituted benzalkonium salt; a mono-cationic compound such as a benzethonium salt and, besides, a poly-cationic compound such as an N-alkyl-N,N,N',N',N'-pentamethyl-propylene ammonium salt. Among them, an alkyl trimethyl ammonium salt, a dialkyl dimethyl ammonium salt, an alkyl dimethyl benzyl ammonium salt or a substituted benzalkonium salt is preferable. Lauryl trimethyl ammonium chloride, stearyl trimethyl ammonium chloride, cetyl trimethyl ammonium chloride, distearyl dimethyl ammonium chloride, a dialkyl ($C_{12}$–$C_{18}$) dimethyl ammonium chloride or an alkyl ($C_{12}$–$C_{14}$) dimethyl benzyl ammonium chloride is particularly preferable.

It is preferable that the surfactant (d) is used in the amount as compared with tetraacetylethylenediamine (b) in terms of the ratio of (b)/(d) of from 20/1 to 2/1 by weight.

When the composition of the present invention is in a solid form such as a powder, a granule or a tablet, it is used as an aqueous solution at a time for use. In case of the virucide composition of the present invention, the concentration thereof is preferably in such concentration that the concentration of the organic peracid is made 160 to 3200 ppm. In case of the sporicide composition of the present invention, the concentration thereof is preferably in such concentration that the concentration of the organic peracid is made 250 to 2000 ppm. Then, the pH of the aqueous solution is preferably 2 to 9, more preferably 4 to 9, further preferably 6 to 8 and particularly preferably 6.5 to 7.5. Adjustment of the pH of the aqueous solution can be achieved by an inorganic acid or an organic acid, and the inorganic acid or the organic acid may be previously added to the solid composition or the inorganic acid or the organic acid may be added to the aqueous solution. In case the acid is previously added to the solid composition as in the former case, the rate of dissolving the acid can be adjusted by coating the acid with a water-soluble substance such as a water-soluble inorganic salt. It is also possible to conduct the coating by means of the above-mentioned component (c).

The composition of the present invention is suitable for virus-killing and/or spore-killing of instruments and furnishings used in medical institutions, etc. Then, it is particularly useful as a virucide composition and/or a sporicide composition for medical devices and instruments including a device or an instrument, for an operation, such as a surgical knife, a scissors and a surgical clamp; a device or an instrument, for a diagnosis, such as endoscope; and a device or an instrument, for a cure, such as an instrument for blood transfusion and a device for dialysis.

Incidentally, the term "sporicidal" used in the present invention means to completely kill germs which can produce spores and which are in the rest stage or the resisting form.

In accordance with the present invention, it is possible to obtain a virucide and/or sporicide composition having its high virucidal effect and/or sporicidal effect and also being excellent in safety and workability.

EXAMPLES

Preparation of the Compositions

The compositions as shown in Table 1 were prepared.

TABLE 1

|  | Examples | | | | | Comparative Examples | | |
| --- | --- | --- | --- | --- | --- | --- | --- | --- |
|  | 1 | 2 | 3 | 4 | 5 | 1 | 2 | 3 |
| Components of compositions (% by weight) | | | | | | | | |
| Sodium percarbonate | 35 | 35 | 35 | 35 | 35 | 100 | 0 | 50 |
| Tetraacetyl ethylenediamine | 35 | 35 | 35 | 35 | 35 | 0 | 0 | 50 |

TABLE 1-continued

|  | Examples | | | | | Comparative Examples | | |
| --- | --- | --- | --- | --- | --- | --- | --- | --- |
|  | 1 | 2 | 3 | 4 | 5 | 1 | 2 | 3 |
| Sodium sulfate | 15 | 10 | 10 | 10 | 10 | 0 | 0 | 0 |
| Magnesium sulfate | 15 | 10 | 10 | 10 | 10 | 0 | 0 | 0 |
| Sodium laurylsulfate *1 | 0 | 10 | 0 | 0 | 0 | 0 | 0 | 0 |
| Polyoxyethylene lauryl ether *2 | 0 | 0 | 10 | 0 | 0 | 0 | 0 | 0 |
| Laurylbetaine *3 | 0 | 0 | 0 | 10 | 0 | 0 | 0 | 0 |
| Peracetic acid solution *4 | 0 | 0 | 0 | 0 | 0 | 0 | 100 | 0 |
| Dialkyl ($C_{12}$–$C_{18}$) dimethylammonium chloride *5 | 0 | 0 | 0 | 0 | 10 | 0 | 0 | 0 |

(Note)
*1: Tradename of EMAL O [manufactured by Kao Corp.]
*2: Tradename of EMULGEN 109P [manufactured by Kao Corp.]
*3: Tradename of AMPHITOL 20BS [manufactured by Kao Corp.]
*4: Consisting of 7% by weight of peracetic acid, 8% by weight of hydrogen peroxide, 34% by weight of acetic acid and the balance of water.
*5: Tradename of QUARTAMIN D2345P [manufactured by Kao Corp.]

Test on the Virucidal Property

The following test on the virucidal property was carried out using the compositions shown in Table 1. The result is shown in Tables 2 and 3 as Test Examples 1 to 5 and Comparative Test Examples 1 to 3.

<Viruses for use>
① Poliovirus: poliovirus type 3, vaccine strain (Sabin strain)
② Herpes simplex virus: HF strain
   FL cells were used for the measurement of growth and infection value of the virus.

<Test Method>
① Each of the compositions as shown in Table 1 was diluted with a sterilized water to the concentration as shown in Tables 2 and 3 to prepare the preparations for the poliovirus and for the herpes simplex virus. All of Examples 1 to 5 and Comparative Example 3 were adjusted to pH 7.0 with citric acid. The concentration of the organic peracid in each of the preparation was 160 to 3200 ppm for Examples 1 to 5 and Comparative Example 3 and was 210 to 3500 ppm for Comparative Example 2. No organic peracid was produced for Comparative Example 1. The method for quantitating the concentration of the organic peracid is as follows.

<Method for Quantitating the Concentration of the Organic Peracid>

(α) A method for Quantitating the Hydrogen Peroxide
About 2 g of the diluted preparation are precisely weighed in a conical beaker having its capacity of 200 mL, the solution is cooled by adding 10 mL of 20% sulfuric acid and 2 or 3 pieces of ice thereto, and then 1 or 2 drops of a saturated aqueous solution of manganese sulfate as catalyst are added. Further, a titration is carried out using an N/2 solution of potassium permanganate. When the solution colors in pale pink for 1 to 10 seconds, the titration is made into finish. The concentration of hydrogen peroxide is calculated by the following Formula (1-1).

$$\text{Hydrogen peroxide } (\%) = \frac{0.85 \times T_1 \times F_1}{W_1} \quad (1\text{-}1)$$

$T_1$: Amount (mL) required for the titration of potassium permanganate $F_1$: Factor of potassium permanganate $W_1$: Weight (g) of the preparation (β) Method for Quantitating the Organic Peracid About 1 g of the diluted preparation is precisely weighed in an Erlenmeyer flask having its capacity of 300 mL and having its connective stopper therewith. Then, 10 mL of 20% sulfuric acid, 20 mL of pure water and 2 mL of a saturated aqueous solution of potassium iodide are added thereto and the flask is tightly closed and gently shaken. This is allowed to quietly stand in a cool and dark place for 5 minutes and then titrated with an N/5 solution of sodium thiosulfate. When the solution colors in light yellow, a few drops of a 2% solution of starch were added thereto and the titration is continued. When violet color of the solution disappears, the titration is made into finish. The concentration of the organic peracid is calculated as the concentration of peracetic acid by the following Formula (1-2).

$$\text{Peracetic acid } (\%) = 76 \times \left( \frac{T_2 \times F_2}{100 \times W_2} - \frac{H}{34} \right) \quad (1\text{-}2)$$

$T_2$: Amount (mL) required for the titration of sodium thiosulfate $F_2$: Factor of sodium thiosulfate $W_2$: Weight (g) of the preparation $H$: The concentration (%) of hydrogen peroxide calculated from Formula (1-1)

② 50 μL of each of the preparations were mixed with 50 μL of a virus solution.
③ The resultant mixture was allowed to stand at 25° C. for 30 minutes and then 50 μL of a 2% aqueous solution of sodium thiosulfate were added thereto.
④ The resultant solution as a mixed system of the above-mentioned 3 components was diluted stepwise at the interval of 10-fold to measure the infection value with virus.

Incidentally, 50 μL of a 2% aqueous solution of sodium thiosulfate were added to 50 μL of each of the preparation, the resultant mixture was allowed to stand for 30 minutes and then 50 μL of a virus solution was added thereto to prepare a virus control.

TABLE 2

| | | Poliovirus | | | | |
|---|---|---|---|---|---|---|
| | | Concentration of the preparation (% by weight) | pH of the preparation | Concentration of the organic peracid in the preparation (ppm) | Infection value with the virus ($\log_{10}\text{TCID}_{50}/\text{ml}$) | Virus control |
| Test Examples | Examples | | | | | |
| 1 | 1 | 2.0 | 7.0 | 3200 | Less than 1.5 | 7.5 |
| | | 0.2 | 7.0 | 320 | 5.0 | 7.5 |
| 2 | 2 | 2.0 | 7.0 | 3200 | Less than 1.5 | 7.5 |
| | | 0.2 | 7.0 | 320 | 5.0 | 7.5 |
| 3 | 3 | 2.0 | 7.0 | 3200 | Less than 1.5 | 7.5 |
| | | 0.2 | 7.0 | 320 | 5.0 | 7.5 |
| 4 | 4 | 2.0 | 7.0 | 3200 | Less than 1.5 | 7.5 |
| | | 0.2 | 7.0 | 320 | 5.0 | 7.5 |
| 5 | 5 | 2.0 | 7.0 | 3200 | Less than 1.5 | 7.5 |
| | | 0.2 | 7.0 | 320 | 5.0 | 7.5 |
| Comparative Test Examples | Comparative Examples | | | | | |
| 1 | 1 | 2.0 | 11.0 | — | 7.5 | 7.5 |
| | | 0.2 | 11.0 | — | 7.5 | 7.5 |
| 2 | 2 | 5.0 | 4.0 | 3500 | 2.0 | 7.5 |
| | | 0.5 | 4.0 | 350 | 6.75 | 7.5 |
| 3 | 3 | 1.4 | 7.0 | 3200 | 2.0 | 7.5 |
| | | 0.2 | 7.0 | 460 | 6.5 | 7.5 |

\* The concentration of the organic peracid in the preparation was determined in terms of the concentration of the peracetic acid (that is the same in the succeeding cases as well).

TABLE 3

| | | Herpes simplex virus | | | | |
|---|---|---|---|---|---|---|
| | | Concentration of the preparation (% by weight) | pH of the preparation | Concentration of the organic peracid in the preparation (ppm) | Infection value with the virus ($\log_{10}\text{TCID}_{50}/\text{ml}$) | Virus control |
| Test Examples | Examples | | | | | |
| 1 | 1 | 1.0 | 7.0 | 1600 | Less than 1.9 | 6.7 |
| | | 0.1 | 7.0 | 160 | Less than 1.9 | 6.7 |
| 2 | 2 | 1.0 | 7.0 | 1600 | Less than 1.9 | 6.7 |
| | | 0.1 | 7.0 | 160 | Less than 1.9 | 6.7 |
| 3 | 3 | 1.0 | 7.0 | 1600 | Less than 1.9 | 6.7 |
| | | 0.1 | 7.0 | 160 | Less than 1.9 | 6.7 |
| 4 | 4 | 1.0 | 7.0 | 1600 | Less than 1.9 | 6.7 |
| | | 0.1 | 7.0 | 160 | Less than 1.9 | 6.7 |
| 5 | 5 | 1.0 | 7.0 | 1600 | Less than 1.9 | 6.7 |
| | | 0.1 | 7.0 | 160 | Less than 1.9 | 6.7 |
| Comparative Test Examples | Comparative Examples | | | | | |
| 1 | 1 | 1.0 | 11.0 | — | 6.5 | 6.7 |
| | | 0.1 | 11.0 | — | 6.7 | 6.7 |
| 2 | 2 | 2.5 | 4.0 | 1750 | Less than 1.9 | 6.7 |
| | | 0.3 | 4.0 | 210 | Less than 1.9 | 6.7 |
| 3 | 3 | 0.7 | 7.0 | 1600 | Less than 1.9 | 6.7 |
| | | 0.1 | 7.0 | 230 | 2.5 | 6.7 |

\* The concentration of the organic peracid in the preparation was determined in terms of the concentration of the peracetic acid.

From the result of Tables 2 and 3, it is recognized that the preparations of Examples 1 to 5 are more excellent in inhibitory property from both infections with poliovirus and herpes simplex virus than those of Comparative Examples 1 to 3.

Test on the Sporicidal Property

The following test on the sporicidal property was carried out using the compositions as shown in Table 1. The result is shown in Table 4 as Test Examples 6 to 10 and Comparative Test Examples 4 to 6.

<Spores for the Test>

*Bacillus cereus* (IFO 13494, being shown in LIST OF CULTURE, MICROORGANISMS $_{10}$TH EDITION 1996 published by INSTITUTE FOR FERMENTATION, OSAKA at 17-85, Juso-honmachi 2-chome, Yodogawa-ku, Osaka 532, Japan) was heated by a conventional manner and the obtained spores were used for the test.

<Test Method>

The sporicide compositions as shown in Table 1 were diluted stepwise by a sterilized water into 5 to 0.1 % by weight to make preparations. The above-mentioned spore was added in the concentration of $1.0 \times 10^7$ celles/mL to each of the preparations. Incidentally, all of Examples 1 to 5 and Comparative Example 3 were adjusted to pH 7.0 with citric acid.

The resultant solution was allowed to stand at 25° C. for 30 minutes, 100 μL from this solution were taken, 0.9 ml of a 1% aqueous solution of sodium thiosulfate was added thereto to inactivate the preparation, and 5 μL of the resultant mixture were inoculated to an incubating medium (200 μL of an SCDLP medium) and incubated at 35° C. Then, the minimum lethal concentration (MLC) was determined. The concentration of the produced organic peracid in each of the preparations was 150 to 8000 ppm and then the concentration of the produced organic peracid in the preparation showing the MLC is shown in Table 4.

<Method for quantitating the Concentration of the Organic Peracid>

Here, the method for quantitating the concentration of the organic peracid in <<Test on the sporicidal property>> is according to the method for quantitating the concentration of the organic peracid described in the above-mentioned <<Test on the virucidal property>>.

TABLE 4

| | | | MLC (% by weight) | pH of the preparation | Concentration of the organic peracid in the preparation showing the MLC |
|---|---|---|---|---|---|
| Test Examples | 6 | Examples 1 | 0.15 | 7.0 | 250 ppm |
| | 7 | 2 | 0.15 | 7.0 | 240 ppm |
| | 8 | 3 | 0.15 | 7.0 | 240 ppm |
| | 9 | 4 | 0.15 | 7.0 | 240 ppm |
| | 10 | 5 | 0.15 | 7.0 | 240 ppm |
| Test Comparative Examples | 4 | Comparative Examples 1 | Ineffective | 11.0 | — |
| | 5 | 2 | 3.5 | 4.0 | 2500 ppm |
| | 6 | 3 | 0.20 | 7.0 | 450 ppm |

* The concentration of the organic preacid in the preparation was determined as the concentration of the preacetic acid.

From the result of Table 4, it is recognized that the preparations of Examples 1 to 5 are more excellent in the sporicidal effect than those of Comparative Examples 1 to 3.

What is claimed is:

1. A virucide and/or sporicide composition comprising (a) sodium percarbonate, (b) tetraacetylethylenediamine and (c) at least one selected from the group consisting of sodium sulfate and an alkaline earth metal salt of an inorganic acid, at a ratio of (a)/(b) by weight of from 1/1 to 2/1 and a ratio of (a)/(c) by weight of from 1/1 to 4/1.

2. The composition as claimed in claim 1, which comprises (d) at least one surfactant selected from the group consisting of a nonionic surfactant, an anionic surfactant, an amphoteric surfactant and a cationic surfactant.

3. A method of killing a virus, which comprises applying an aqueous solution containing the composition as defined in claim 1 on a place where a virus can be killed.

4. A method of killing a spore which comprises applying an aqueous solution containing the composition as defined in claim 1 on a place where a spore can be killed.

5. The composition as claimed in claim 3, wherein the ratio of (a)/(b) by weight is from 1/1 to 2/1, and a ratio of (b)/(d) by weight is from 20/1 to 2/1.

6. The composition as claimed in claim 1, wherein the alkaline earth metal salt of an inorganic acid is selected from the group consisting of magnesium sulfate, magnesium nitrate, magnesium chloride, and magnesium carbonate.

7. The composition as claimed in claim 6, wherein the alkaline earth metal salt of an inorganic acid is magnesium sulfate.

8. A virucide and/or sporicide composition comprising (a) sodium percarbonate, (b) tetraacetylethylenediamine and (c) at least one selected from the group consisting of sodium sulfate and an alkaline earth metal salt with an inorganic acid at the ratio of (a)/(b) by weight being from 1 to 2/1, a ratio of (a)/(c) by weight of from 1/1 to 4/1, and wherein the composition is in a solid form.

9. The composition as claimed in claim 8, wherein the composition is in a solid form selected from the group consisting of a tablet, a granule and a powder.

10. The composition as claimed in claim 8, which comprises (d) at least one surfactant selected from the group consisting of a nonionic surfactant, an anionic surfactant, an amphoteric surfactant and a cationic surfactant.

11. A method of killing a virus, which comprises applying an aqueous solution containing the composition as defined in claim 8 on a,place where a virus can be killed.

12. A method of killing a spore, which comprises applying an aqueous solution containing the composition as defined in claim 8 on a place where the spore can be killed.

13. The composition as claimed in claim 10, wherein the ratio of (a)/(b) by weight is from 1/1 to 2/1, and a ratio of (b)/(d) by weight is from 20/1 to 2/1.

14. A method of killing a virus or a spore, which comprises:

applying an aqueous solution of a virucide and/or sloricide composition containing (a) sodium percarbonate, (b) tetraacetylethylenediamine and (c) at least one selected from a salt of an alkaline metal of an inorganic acid and a salt of an alkaline earth metal of an inorganic acid, at a ratio of (a)/(b) by weight of from 10/1 to 1/2.

15. A method of killing a virus or a spore, which comprises:

applying an aqueous solution of a virucide and/or sporicide composition containing (a) an inorganic peroxide, (b) tetraacetylethylenediamine and (c) at least one selected from a salt of an alkaline metal of an inorganic acid and a salt of an alkaline earth metal of an inorganic acid, at a ratio of (a)/(b) by weight of from 1/1 to 2/1.

16. A method of killing a virus or a spore, which comprises:, applying an aqueous solution of a virucide and/or sporicide composition containing (a) sodium percarboiate, (b) tetraacetylethylenediamine and (c) at least one selected from a salt of an alkaline metal of an inorganic acid and a salt of an alkaline earth metal of an inorganic acid, at a ratio of (a)/(b) by weight of from 1/1 to 2/1.

17. A virucide and/or sporicide composition comprising (a) sodium percarbonate, (b) telraacetylethylenediamine and (c) at least one selected from the group consisting of sodium sulfate, sodium nitrate and sodium chloride, wherein when (c) is sodium nitrate and/or sodium chloride then (a)/(b) is in a ratio by weight of from 10/1 to 1/2 and (a)/(c) is in a ratio by weight of from 1/1 to 4/1, and wherein when (c) is sodium sulfate then (a)/(b) is in a ratio by weight of from 1/1 to 2/1 and (a)/(c) is in a ratio by weight of from 1/1 to 4/1.

* * * * *